United States Patent [19]

Peterson

[11] 4,176,412
[45] Dec. 4, 1979

[54] URINE COLLECTION DEVICE

[75] Inventor: James J. Peterson, Elgin, Ill.

[73] Assignee: The Kendall Company, Boston, Mass.

[21] Appl. No.: 942,524

[22] Filed: Sep. 15, 1978

[51] Int. Cl.² .......................................... E03D 13/00
[52] U.S. Cl. ..................................................... 4/144.1
[58] Field of Search ................. 73/421 R; 4/242, 243, 4/144.1, 144.2; 128/2 F; 141/331, 340

[56] References Cited

U.S. PATENT DOCUMENTS

| 661,681 | 11/1900 | Ashbaugh | 141/340 |
|---|---|---|---|
| 3,161,891 | 12/1964 | Bauman | 4/144.1 |
| 3,711,871 | 1/1973 | Sherin | 4/144.1 |
| 3,777,739 | 12/1973 | Raitto | 128/2 F |
| 3,881,465 | 5/1975 | Raitto | 128/2 F |

OTHER PUBLICATIONS

Sani Catch-A Sales Brochure of Concord Laboratories, 144 Davis St., Keene, NH 03431, Cat. No. 1000.
Bard Mid-Stream Urine Collector, Bard Hospital, Div. C. R. Bard, Inc., Murray Hill, N.J. 07971, 1973.

Primary Examiner—S. Clement Swisher
Attorney, Agent, or Firm—Powell L. Sprunger

[57] ABSTRACT

A device for collecting the mid-stream portion of a urine discharge comprising, a receptacle having a lower wall and a side wall defining a cavity, with the receptacle having an upper rim defining an opening communicating with the cavity. The device has a protective member comprising a retaining portion having an inner circumferential flange and an outer circumferential flange connected to the inner flange, with the inner and outer flanges being spaced from each other a distance approximately equal to the thickness of the receptacle rim such that the inner and outer flanges define an annular groove to snugly receive the container rim. The protective member has an outwardly flared skirt depending from the outer flange and extending around at least a substantial portion of the receptacle when the receptacle rim is received in the retaining groove. The protective member also has an outwardly directed handle to facilitate manipulation of the device.

7 Claims, 4 Drawing Figures

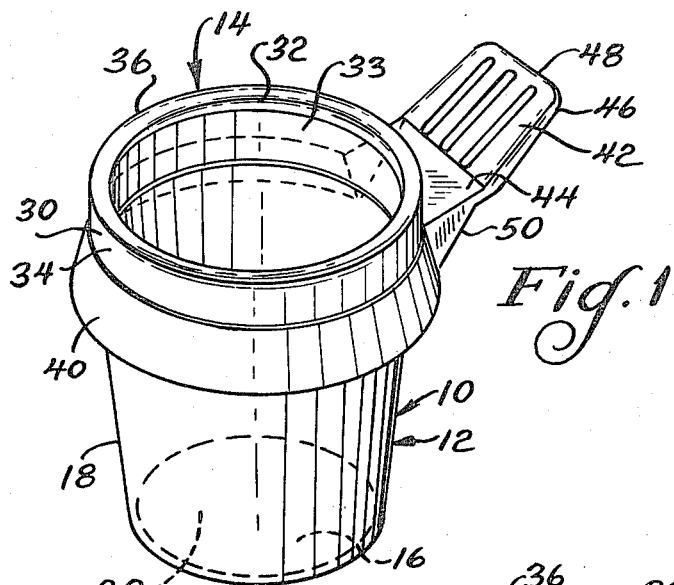
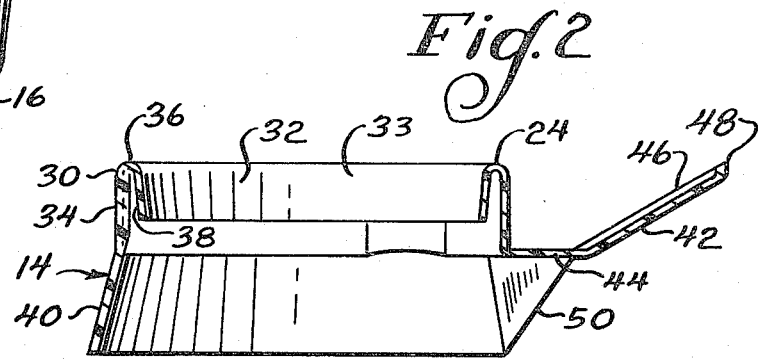
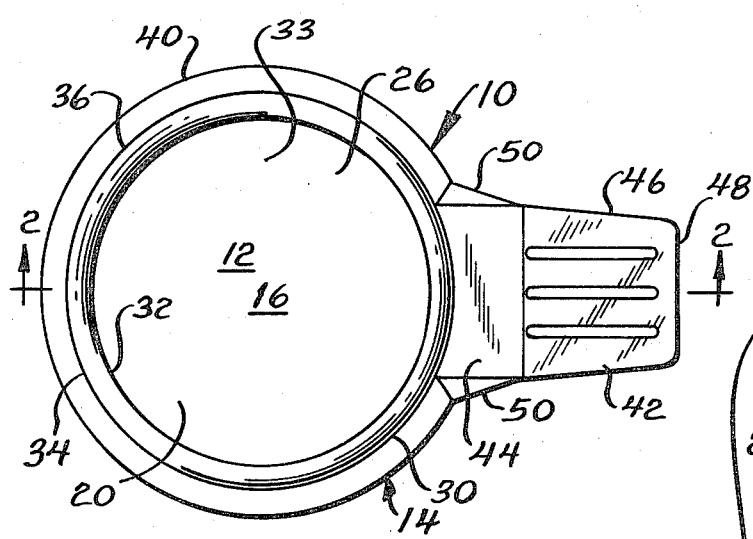
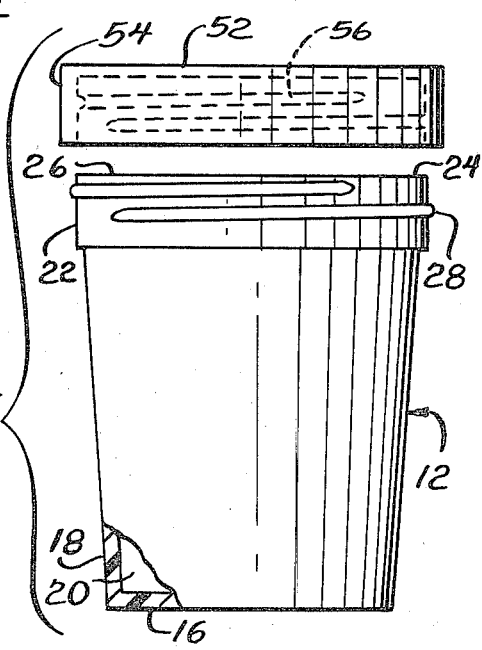

URINE COLLECTION DEVICE

BACKGROUND OF THE INVENTION

The present invention relates to urine collection devices.

It has become common practice to obtain and analyze urine samples from patients for use in diagnosing the patients. Of course, it is necessary to minimize the possibility that the sample may be contaminated, else the laboratory results will be deleteriously affected. In this regard, it is desirable that only the mid-stream portion of the urine discharge be collected for analysis, since the initial portion of the discharge may be contaminated by the patient's body itself. However, such a procedure is particularly difficult for female patients, and the patient may contaminate the specimen or container during manipulation of the container in an attempt to capture the mid-stream portion of the discharge. Further, it is desired that the container permits collection of the sample without wetting of the patient's hands or the outside of the container during voiding.

SUMMARY OF THE INVENTION

A principal feature of the present invention is the provision of a device of simplified construction for collecting the mid-stream portion of a urine discharge.

The device of the present invention comprises a receptacle having a lower wall and a side wall defining a cavity with the receptacle having an upper rim defining an opening communicating with the cavity. The device has a protective member comprising a retaining portion having an inner circumferential flange and an outer circumferential flange connected to the inner flange, with the inner and outer flanges being spaced from each other a distance approximately equal to the thickness of the receptacle rim such that the inner and outer flanges define an annular groove to snugly receive the container rim. The protective member has an outwardly flared skirt depending from the outer flange and extending around at least a substantial portion of the receptacle when the receptacle rim is received in the retaining groove. The protective member also has an outwardly directed handle.

A feature of the present invention is that the handle facilitates manipulation of the device during collection of a mid-stream portion of the urine discharge without wetting of the user's hands.

Still another feature of the invention is that the inner and outer flanges retain the rim of the container such that the protective member supports the receptacle during collection of the discharge.

Yet another feature of the invention is that the retaining portion covers the inner and outer surfaces of the receptacle rim to prevent contamination of the receptacle and sample during manipulation of the device.

A feature of the present invention is that the skirt prevents wetting of the outside of the container during collection of the sample.

Thus, the protective member minimizes the possibility that the attendant may be required to handle a wetted container which otherwise may be offensive to the attendant and may result in cross-contamination from the patient's urine to the attendant.

A further feature of the invention is that the protective member may be readily removed from the receptacle without contamination of the sample after voiding has been completed.

Still another feature of the invention is the provision of a lid for closing the receptacle and permit convenient shipment of the sample to a laboratory for analysis.

Further features will become more fully apparent in the following description of the embodiments of this invention and from the appended claims.

DESCRIPTION OF THE DRAWINGS

In the drawings:

FIG. 1 is a perspective view of a urine collection device of the present invention;

FIG. 2 is a sectional view of a protective member for the device of FIG. 1;

FIG. 3 is a top plan view of the device of FIG. 1; and

FIG. 4 is an exploded view, taken partly in section, illustrating use of a cap to close a receptacle of the device of FIG. 1.

DESCRIPTION OF THE PREFERRED EMBODIMENTS

Referring now to FIGS. 1–4, there is shown a urine collection device generally designated 10 having a receptacle 12 and a protective member 14. The receptacle 12 has a lower wall 16 and a tapered annular side wall 18 defining a cavity 20 in the receptacle 12. The receptacle 12 also has an upper annular rim 22 defining an upper edge 24 of the receptacle 12 and an opening 26 communicating with the cavity 20. As shown in FIG. 4, the receptacle 20 may have suitable threads 28 surrounding the rim 22 for a purpose which will be described below.

With reference to FIGS. 1–3, the protective member 14 has a retaining portion 30 comprising an inner circumferential flange 32 defining an opening 33 to receive the urine discharge, an outer circumferential flange 34, and an upper edge 36 connecting the inner and outer flanges 32 and 34 and maintaining the flanges in a spaced relationship to define an annular groove 38 intermediate the flanges 32 and 34. The inner and outer flanges 32 and 34 are spaced apart a distance approximately equal to the thickness of the receptacle rim 22, such that the retaining portion groove 38 snugly receives the receptacle rim 22. The protective member 14 also has an outwardly flared skirt 40 depending from the outer flange 34 and extending substantially around the receptacle 12 when attached to the protective member.

The protective member 14 has an outwardly directed handle 42 comprising an inner connecting portion 44 which extends generally perpendicular from a lower edge of the outer flange 34, and an outer end portion 46 extending upwardly from and at an acute angle relative to the connecting portion 44. In a preferred form, as shown, an outer end edge 48 of the end portion 46 is generally aligned with the upper edge 36 of the retaining portion 30. Further, the protective member 14 has a pair of spaced reinforcement flanges 50 extending between sides of the connecting portion 44 and the skirt 40 to provide stability to the handle 42 during use. The receptacle 12 and protective member 14 may be made from any suitable plastic material, and, in a preferred form, the receptacle 12 is transparent.

With reference to FIG. 4, the device also has a lid or cap 52 having a depending annular flange 54. The flange 54 has inner threads 56 which cooperate with the threads 28 on the receptacle rim 22 in order to releasably secure the lid 52 onto the receptacle 12 and close the cavity opening 26.

The device is supplied in a sterile condition to the physician, and, in a preferred form, the protective member 14 is pre-attached to the receptacle 12 in a suitable tray with the receptacle rim 22 releasably received in the protective member groove 38. Although the device may be utilized for collection of a urine specimen from a male patient, the device is particularly advantageous for use by a female patient. Preparatory to collection of the sample, the patient spreads and cleanses the labia, and then begins to void. After the initial portion of the discharge has been voided, the patient positions the device into the urine stream such that the mid-stream portion of the urine discharge passes through the protective member into the receptacle for collection therein. After voiding has been completed, the protective member 14 is removed from the receptacle 12, and the lid 52 is secured onto the receptacle rim 22 in order to close the cavity of the receptacle. The closed receptacle may then be shipped to the laboratory and stored until analysis of the sample has been completed.

Thus, in accordance with the present invention, the protective member covers the inner and outer side surfaces of the receptacle rim in order to prevent contamination to the receptacle in this region which otherwise may result in contamination of the sample. Further, the protective member provides a convenient handle to facilitate manipulation of the device during collection of the mid-stream portion of the urine discharge without wetting of the patient's hands. The skirt of the protective member minimizes the possibility that the outer side surface of the receptacle may become wetted during voiding of the discharge, thus alleviating the possibility that the attendant may be required to handle a wetted receptacle which may otherwise be both offensive and may result in cross-contamination from the sample to the attendant. The device also permits convenient removal of the protective member from the receptacle without contamination of the sample, and closure of the receptacle by the lid for subsequent storage of the sample prior to analysis.

The foregoing detailed description is given for clearness of understanding only, and no unnecessary limitations should be understood therefrom, as modifications will be obvious to those skilled in the art.

I claim:

1. A device for collecting the mid-stream portion of a urine discharge, comprising:
a receptacle having a lower wall and a side wall defining a cavity, said receptacle having an upper rim defining an opening communicating with the cavity; and
a protective member comprising a retaining portion having an inner circumferential flange and an outer circumferential flange connected by an upper edge to said inner flange, with said inner and outer flanges being spaced from each other a distance approximately equal to the thickness of the receptacle rim such that said inner and outer flanges define an annular groove to snugly receive the container rim, and with said retaining portion having a generally U-shape in cross-section and defining an upper portion of the protective member in the region of the receptacle rim, said protective member having an outwardly flared skirt depending from said outer flange and extending around at least a substantial portion of the receptacle and being closely spaced from the receptacle sidewall when the receptacle rim is received in the retaining groove, with said skirt having a lower edge extending around the receptacle sidewall beneath said retaining portion of the protective member, said protective member having an outwardly directed handle to facilitate manipulation of the device.

2. The device of claim 1 including a cap for closing the receptacle opening when the protective member is removed from the receptacle, and means for releasably attaching the cap to the receptacle rim over said opening.

3. The device of claim 2 wherein the attaching means comprises cooperating threads on said cap and rim.

4. The device of claim 1 wherein said handle projects from a lower end of said outer flange.

5. A device for collecting the mid-stream portion of a urine discharge, comprising:
a receptacle having a lower wall and a side wall defining a cavity, said receptacle having an upper rim defining an opening communicating with the cavity; and
a protective member comprising a retaining portion having an inner circumferential flange and an outer circumferential flange connected to said inner flange, with said inner and outer flanges being spaced from each other a distance approximately equal to the thickness of the receptacle rim such that said inner and outer flanges define an annular groove to snugly receive the container rim, said protective member having an outwardly flared skirt depending from said outer flange and extending around at least a substantial portion of the receptacle when the receptacle rim is received in the retaining groove, said protective member having an outwardly directed handle to facilitate manipulation of the device, with said handle having a first outwardly directed connecting portion, and an end portion extending upwardly from the connecting portion.

6. The device of claim 5 wherein an outer edge of said end portion is generally aligned with an upper end of said retaining portion.

7. The device of claim 5 including a pair of spaced reinforcement flanges extending between said connecting portion and said skirt.

* * * * *